(12) United States Patent
Beam et al.

(10) Patent No.: US 7,166,259 B2
(45) Date of Patent: Jan. 23, 2007

(54) AIR PURIFIER WITH CONTROL SENSORS

(75) Inventors: R. Paul Beam, Knoxville, TN (US); James Normark, Mt. Carmel, TN (US); David Sutton, Greeneville, TN (US); Tom Greene, Morristown, TN (US); Neal Morris, Greeneville, TN (US)

(73) Assignee: EcoQuest International, Inc., Greeneville, TN (US)

( * ) Notice: Subject to any disclaimer, the term of this patent is extended or adjusted under 35 U.S.C. 154(b) by 0 days.

(21) Appl. No.: 10/918,323

(22) Filed: Aug. 13, 2004

(65) Prior Publication Data

US 2006/0034737 A1 Feb. 16, 2006

(51) Int. Cl.
*B01J 19/08* (2006.01)
(52) U.S. Cl. .................. 422/186.04; 422/186.07; 422/186.03; 422/121
(58) Field of Classification Search ............ 422/186.3, 422/186.07, 186.04, 121
See application file for complete search history.

(56) References Cited

U.S. PATENT DOCUMENTS

| | | | | |
|---|---|---|---|---|
| 4,861,356 A | * | 8/1989 | Penney | 96/77 |
| 5,173,268 A | * | 12/1992 | Weaver | 422/186.15 |
| 5,203,989 A | * | 4/1993 | Reidy | 210/137 |
| 5,656,063 A | * | 8/1997 | Hsu | 95/58 |
| 5,689,261 A | | 11/1997 | Mehta et al. | 341/173 |
| D397,196 S | | 8/1998 | Tsuji | D23/356 |
| 5,933,702 A | * | 8/1999 | Goswami | 422/186.3 |
| 6,022,511 A | * | 2/2000 | Matschke | 422/121 |
| D425,609 S | | 5/2000 | Hyon | D23/359 |
| D429,805 S | | 8/2000 | Hyon | D23/359 |
| 6,135,838 A | * | 10/2000 | Wang | 445/22 |
| 6,616,736 B2 | | 9/2003 | Massey et al. | 96/25 |
| 6,635,153 B1 | | 10/2003 | Whitehead | 204/176 |
| 6,660,070 B2 | | 12/2003 | Chung et al. | 96/424 |
| 6,716,406 B2 | | 4/2004 | Reisfeld et al. | 423/245.1 |
| 6,783,740 B2 | * | 8/2004 | Colby et al. | 422/186.3 |

OTHER PUBLICATIONS

International Search Report, PCT/US2005/008614 (Aug. 30, 2005).
Written Opinion of the International Searching Authority (Aug. 30, 2005).

* cited by examiner

*Primary Examiner*—Kishor Mayekar
(74) *Attorney, Agent, or Firm*—Baker, Donelson, Bearman, Caldwell & Berkowitz, PC

(57) ABSTRACT

An air purifier (10) held in a housing (12, 14) with an ambient air inlet (16) and an air outlet (18) and defining an airflow path therethrough for treating ambient air, a filter (disposed in the airflow path and having an air permeable media for communicating air therethrough while retaining particles carried in the flow of air. A purification device attaches to an intermediate chassis in the airflow path for treating the air moved by a fan (70) into operative engagement with the purification device within the housing and out the air outlet. A controller operates the purification device by sensing an operative status of the purification device.

11 Claims, 4 Drawing Sheets

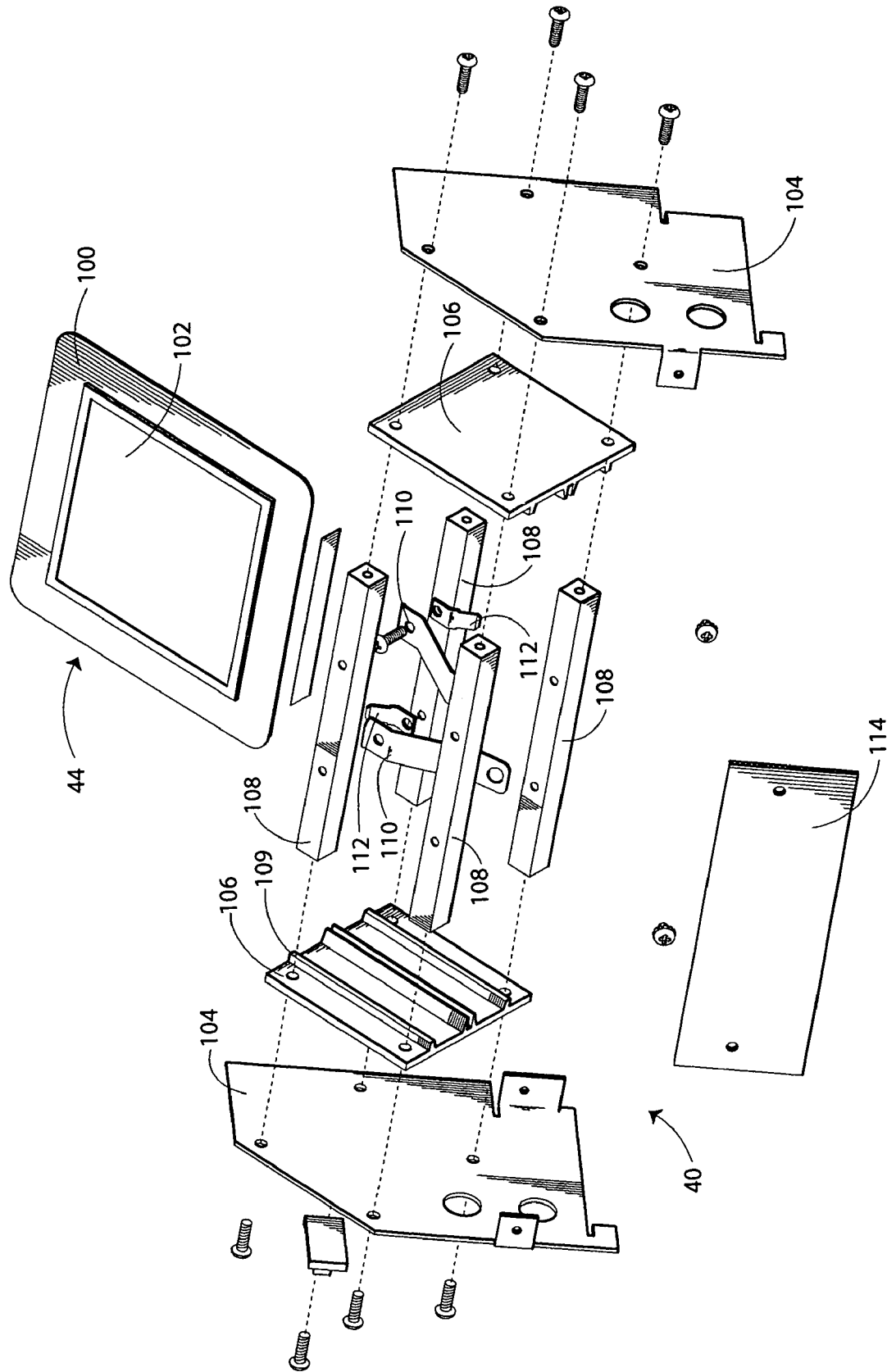

AIR PURIFIER WITH CONTROL SENSORS

TECHNICAL FIELD

The present invention relates to air purifiers. More particularly, the present invention relates to air purifiers with enhanced purification features while sensors monitor and control operation of the air purifier.

BACKGROUND OF THE INVENTION

In recent years, the use of air purifiers has become more popular in interior spaces such as homes and offices. The increasing use of air purifiers results from the perception that air born dust, allergens, and micro-organisms such as germs and bacteria affect the health of persons breathing the air. Increased use of insulation, improved building construction techniques, and closure devices such as windows and doors with tighter tolerances provides buildings with increased resistance to air infiltration. As a result, fresh exterior air is exchanged or introduced to the building in lower volumes such as through open doors, windows, and air handling systems.

While exchange of interior and exterior air is desirable, such exchanges may be impractical to accomplish. Large office buildings, for example, typically re-circulate interior air while mixing a proportion of fresh air into the air handling system. These exchanges of air however increase cooling and heating costs. Accordingly, while fresh air is desirable, the increased cost to maintain a cool or warm temperature lessens the desirability of the air exchange.

Air purifiers used in interior spaces accordingly address the need for providing fresh air by removing odors, dust, and air born pollutants from the interior air. Conventional air purifiers include a blower that pushes or pulls air through a filter element. There are a number of different commercially available types of filters with differing air permeability and thus different filtering characteristics. These include particulate filters to remove larger particles from the air, electrostatic filters to trap particles sensitive to electrostatic charges, and odor filters to remove odors or to scent the air, such as the use of a conventional odor filter including activated carbon or charcoal that remove pollutants primarily by absorption.

In addition to filters, some air purifiers include additional air purification features. These include the use of UV lights for destroying germs and pathogens carried in the air. Other devices generate positive or negative ions which are introduced into the air stream flowing through the air purifier. The ions emitted into the volume of the room tend to electrostatically cling to pollutants having opposing charges. These attached ions increase the weight of the air born particles and cause the heavier particles to fall to the ground, thereby clearing the air of dust and other pollutants.

While these air purifiers have met a need for increased treatment of interior air, there are drawbacks to their use. Periodically, components of the air purifiers need to be replaced. The housings that contain the components however are not readily accessible for replacement and/or cleaning of the components. Further, some devices useful for air purification have not readily been used due to the sophisticated controls necessary to assure proper operation.

Accordingly, a need remains in the art for an air purifier which provides enhanced air purification features while detection sensors monitor and control the operation of the air purifier. It is to the provision of such that the present invention is primarily directed.

SUMMARY OF THE INVENTION

The present invention meets the need in the art by providing an air purifier held in a housing with an ambient air inlet and an air outlet to define an airflow path for treating ambient air. A fan moves the air from the air inlet through the airflow path and out the air outlet. A filter disposed in the airflow path has an air permeable media for communicating air therethrough while retaining particles carried in the flow of air. An ultraviolet light source having non-quartz glass attached to a chassis in the airflow path for treating the air with an emission of ultraviolet light. A photocatalytic screen removably supported in the housing in the airflow path is configured to be exposed to the ultraviolet light source to create hydroxyl radicals for reacting with and neutralizing organic compounds in the flow of air. A purification device attaches to the chassis in the airflow path for treating the air moved by the fan into operative engagement with the purification device within the housing. The purification plate made of a dielectric material and opposing metal mesh screens in electrical communication with a supply of electrical current is configured to generate an electrical spark for creating ozone in the flow of air. An ionizer generates a plurality of ions inserted into the airflow. A controller operates the air purifier by sensing an operative status of the air purifier. A photocell mounts in proximity to the ultraviolet light source. The controller is responsive to a signal from the photocell whereby the air purifier is operative during detection of light from the ultraviolet light source. A current detector configured to sense electrical flow to the metal mesh screens of the purification plate signals the controller if the electrical current is below a first preselected threshold and to signal the controller if the electrical current is above a second preselected threshold, whereby the air purifier is operative if the electrical current to the purification plate is within the preselected range.

Objects, advantages, and benefits of the present invention will become apparent upon reading the following detailed description in view of the drawings and the appended claims.

BRIEF DESCRIPTION OF THE DRAWINGS

FIG. 4 is a perspective exploded view of a cage assembly for a purification device used in the air purifier illustrated in FIG. 1.

DETAILED DESCRIPTION

Figure 1:
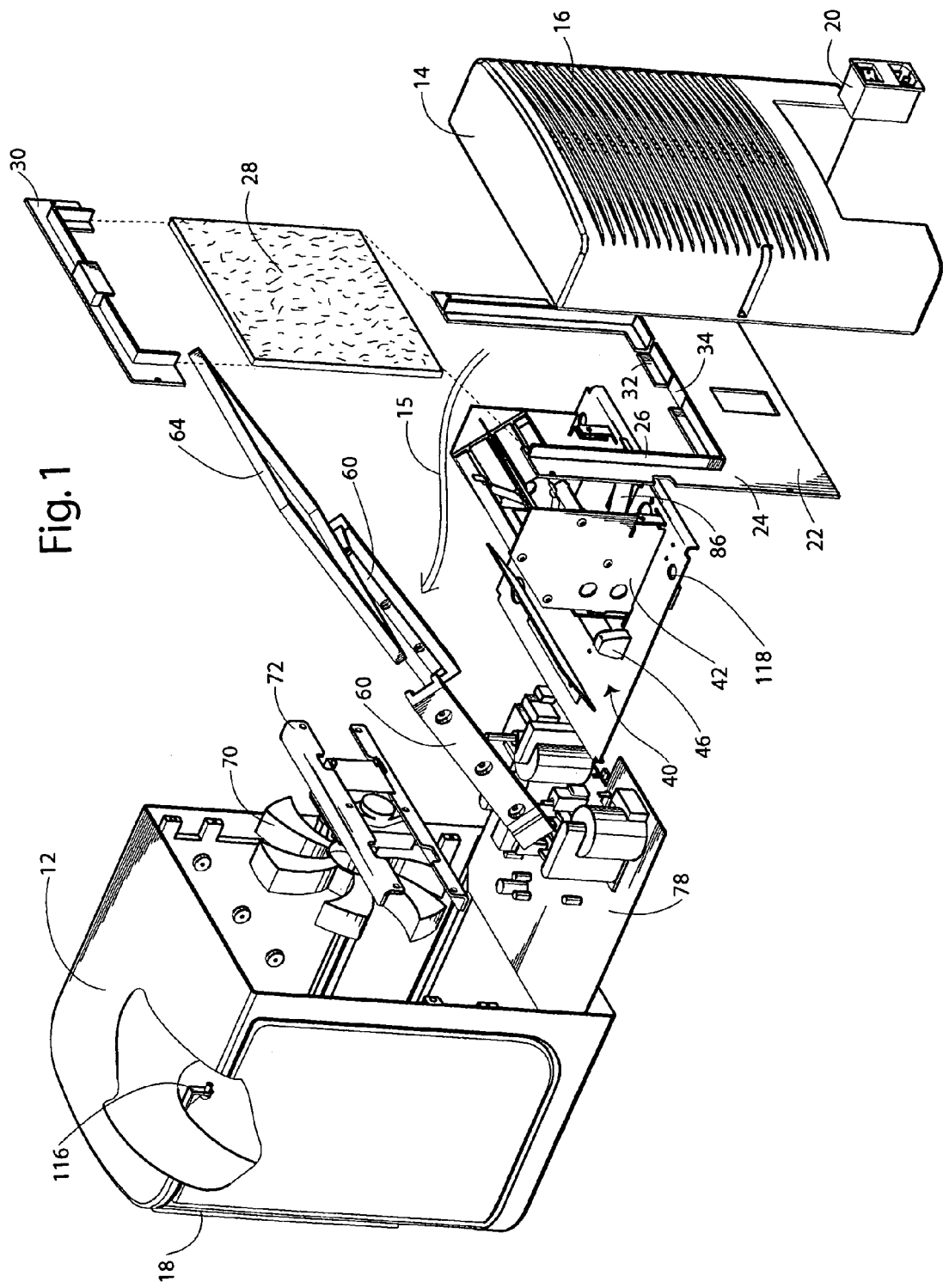
FIG. 1 is a perspective back and right side exploded view of a air purifier according to the present invention providing enhanced air purification features with operation detection sensors.

With reference to the drawings, in which like parts have like identifiers, FIG. 1 illustrates in perspective exploded view an air purifier 10 configured as a portable, self-standing unit for treating air in a room. The air purifier 10 includes a housing having a front cover 12 and a back cover 14 that engage to define an air flow path generally 15 between a grilled air intake 16 in the back cover 14 and a grilled air outlet 18 in the front cover 12. The back cover 14 includes a fuse switch/power block 20 that conventionally includes a fuse, power switch, and electrical contacts for connecting a power cord from a source of electricity for operation of the air purifier 10. The front cover 12 includes a display 21, such as an LCD screen. The display 21 communicates with a controller to display operational and status information for a person using the air purifier 10 to treat air.

A filter frame 22 mounts in the front cover 12. The filter frame 22 includes opposed arms 24 with extending flanges 26. The arms 24 and the flanges 26 cooperatively define guide tracks for receiving a filter element 28. A U-shaped member 30 defines a top of the filter frame 22. Fasteners (not illustrated) secure the member 30 to the arms 24 of the filter frame 22 to hold the filter element 28 in the filter frame. In the illustrated embodiment, the filter frame 22 includes a seat 32 which receives an edge of the filter element 28. A notch 34 is defined in the seat, for a purpose discussed below.

An intermediate chassis 40 supports a cage 42 for a purification plate 44, as discussed in detail below. An ultraviolet (UV) light source 46 mounts to the intermediate chassis 40 adjacent the cage 42. The UV light source 46 includes a UV bulb 48 held by opposing electrical contact supports 50. The UV bulb 48 communicates with a transformer mounted to the intermediate chassis 40 and a starter element 54. A photocell 55 mounts in close proximity to the UV light source and communicates with the controller which detects the operational status of the UW bulb 48.

A pair of opposing support tracks 60 are illustrated exploded from the housing 12. The support tracks are disposed at an oblique angle relative to the flow path 15 through the air purifier 10. The support tracks 60 attach with fasteners to the opposing interior walls of the front cover 12. Each support track 60 includes a central channel 62 for cooperatively receiving and holding a photocatalytic screen 64. The photocatalytic screen 64 comprises a stainless steel mesh 66 impregnated with titanium oxide or a metallic alloy screen that generates hydroxyl radicals in the presence of UV light, such as RCIC-5A, -9A, -9C, -9HOA, -9HOC, -11HOA, -11C, -14C, -14HOA, -14HOC, -36†5 A, -36HOA, and -36UVA, available from RGF Environmental Group, Inc., of West Palm Beach, Fla.

A fan 70 having a motor attaches to a fan support bracket 72. The fan support bracket mounts with fasteners to the interior of the front cover 12 near the grilled air outlet 18. A circuit board chassis 78 mounts in a lower portion of the front cover 12.

Figure 3:
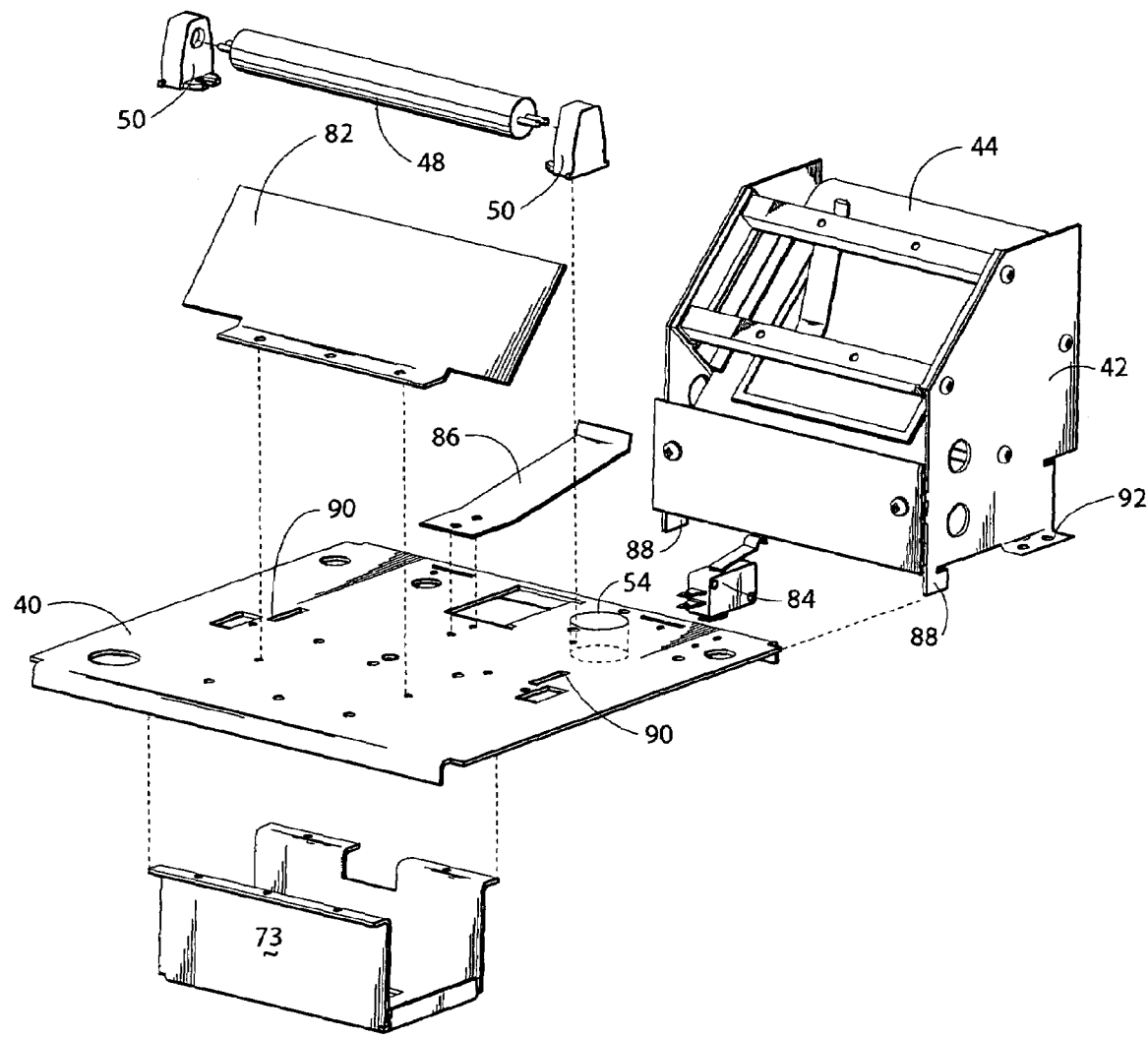
FIG. 3 is a exploded perspective view of a chassis assembly for purification devices used in the air purifier illustrated in FIG. 1.

FIG. 3 illustrates a perspective exploded view of the intermediate chassis 40 and the cage 42. A U-shaped tray 73 mounts to the intermediate chassis 40 and supports a transformer (not illustrated). The electrical contact supports 50 for the UV bulb 48 mount to the chassis 40 in spaced apart relation. A cover plate 82 mounts to the chassis 40 adjacent the bulb 48 with fasteners (not illustrated). A contact switch 84 attaches to a rearward portion of the chassis 40. An arm 86 attaches to the contact switch and extends to the notch 34 in the filter frame 22, for a purpose discussed below. The cage 42 mounts with legs 88 that engage slots 90 in the chassis 40. Lateral flanges 92 on the cage 42 receive fasteners that secure the cage 42 to the chassis 40.

FIG. 4 is an exploded view of the cage 42 that holds the purification plate 44, which provides a corona discharge device for generating ozone. The purification plate 44 includes a ceramic sheet 100 overlayed with stainless steel mesh 102 on opposing major planar sides. The cage 40 includes opposing side panels 104 that support positioning members 106 and interconnect with four spaced-apart parallel cross-arms 108. Fasteners extend through the side 104, the positioning member 106 and into the respective distal ends of the cross-members 108 to rigidly connect the cage together. The positioning members 106 each include spaced-apart flanges 109 that define a slot for receiving the purification plate 44. Two pairs of a contact arm 110 and an electrical connection tab 112 attach in opposing relation to one of the cross-arms 108. The contact arms 110 are metallic strips that angle towards the opposing contact arm. A first of the contact arms 110 contacts the stainless steel mesh 102 on one side of the purification plate 44 and the second of the contact arms 110 contacts the stainless steel mesh on the opposing side. A rear UV shield 114 connects between the opposing panels 104 adjacent the UV light bulb 48.

The air freshner in the illustrated embodiment includes a needle ionizer 116 and an antenna ionizer 118. The needle ionizer 116 mounts to the interior of the housing 12 forwardly of the fan 70. The antenna 116 mounts to the chassis 40. These generate negative ions and positive ions that enter into the airflow and communicate with the purified air into the room. The needle ionizer 116 conventionally operates to create negative ions while a round antenna 118 generates RF and positive ions.

Figure 2:
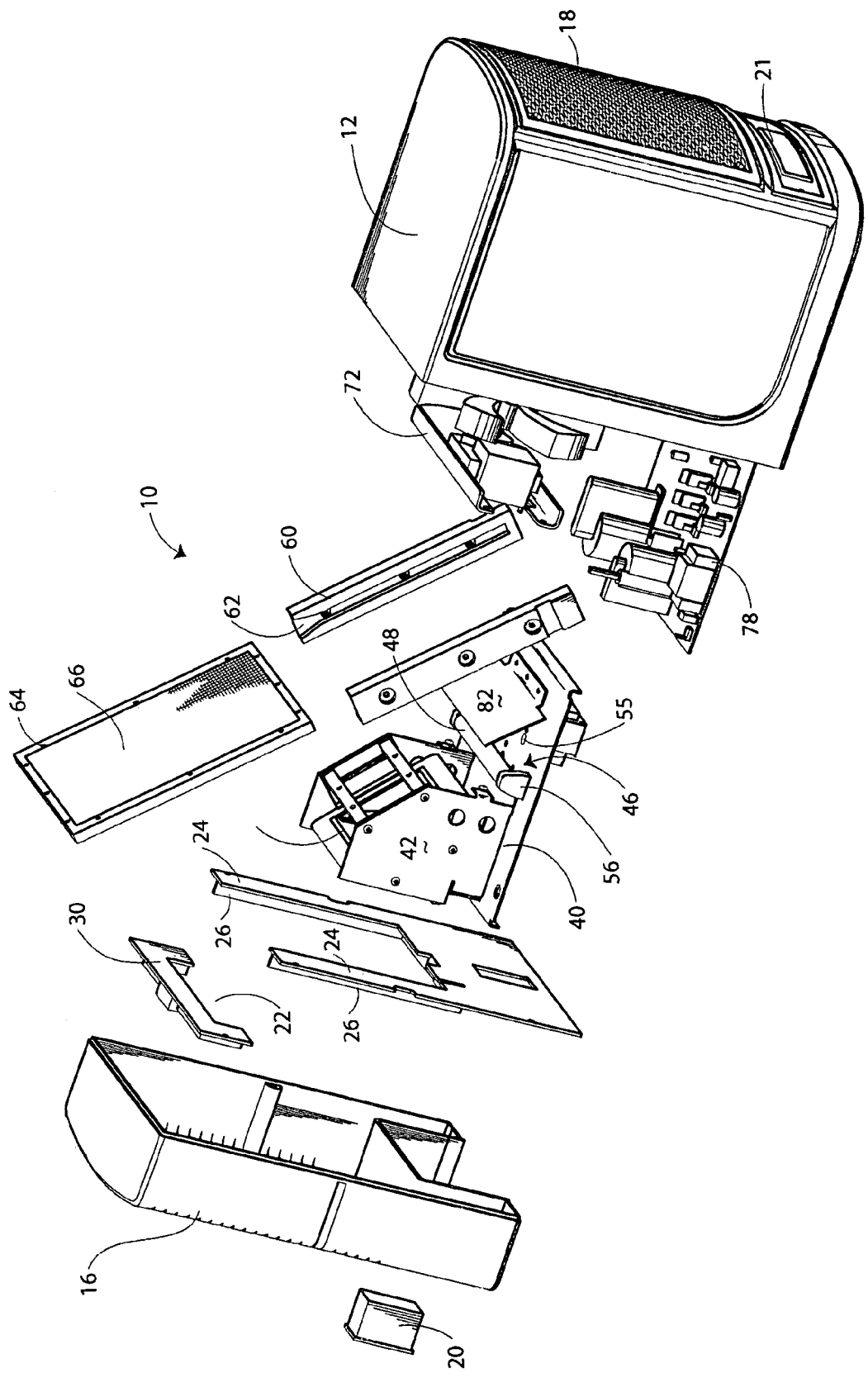
FIG. 2 is a perspective front and left side exploded view of the air purifier illustrated in FIG. 1.

With reference to FIGS. 1 and 2, the air purifier 10 operates to purify air communicated through the air intake 16 and blown by the fan 70 through the air outlet 18 into a room. The air passes through the filter element 28 which traps particulates in the air flow. The UV light emitted from the UV bulb 48 destroys pathogens and other microbes carried in the airflow. The UV light also activates the photocatalytic screen 64. The photocatalytic screen 64 generates hydroxyl radicals. These short lived radicals react with and neutralize volatile organic compounds in the airflow. The arcing of the purification plate 44 generates ozone as a corona-discharge device. The amount or frequency of arcing is correlated to the square footage of the room(s) to receive the purified air. Because the air purifier 10 includes the purification plate 44 for generating ozone, the UV lamp 48 in the illustrated embodiment can be made of non-quartz glass. Positive and negative ions are generated by the needle 116 and the RF antenna 118. The fan 70 blows the air in the air stream through the outlet 18.

In an alternate embodiment, the purification plate 44 comprises part TF347 available from TT Electronics IRC-Advanced Film Division, Corpus Christi, Tex. That purification plate includes a ceramic substrate with a glass coating on opposing major sides and a electrical conductor material (tungsten-based) printed as patches on the surface of the glass coating on the opposing sides. The electrical conductor material is selected for resistance to corrosion by ozone. The opposing patches connect to a supply of electrical current, such as by contacting copper patches applied to the opposing sides with the opposing contact arms 110. The patches may be of consistent size; however, the patch printed on the side exposed to the airflow in the air purifier 10 if smaller in area that of the patch on the opposing side, forces the corona discharge to the side exposed to the air flow.

The air purifier 10 of the present invention provides operation instructions for users based on status information detected by sensors. The edge of the filter element 28 received in the notch 34 operates the contact switch 84 through the arm 86. If the filter element 28 is not properly seated, the switch 84 is not activated. The switch 84, if not closed, prevents electrical current from being communicated to the controller and thus the air purifier 10 is not operative.

The photocell 55 mounted to the chassis in proximity to the UV bulb 48 detects whether the UV bulb is operational. If the UV bulb is burnt out, not installed properly, or insufficiently bright, the controller, coupled to the photocell 55, detects the inoperability of the UV bulb. The controller causes a message to be displayed instructing the user to replace the UV bulb.

The controller includes a sensor that monitors the operational status of the purification plate 44. The sensor measures the RF generated by the arcing of the high voltage applied to the opposing mesh 102. The sensor includes an antenna with an amplifier and comparator to determine whether the EMI or electromagnetic interference is above a preselected threshold. If there is excessive RF, the plate 44 is damaged and requires replacement. The controller causes the display to show a message indicating the purification plate 44 needs to be replaced.

In addition, the sensor monitors the power communicated to the purification plate 44. If the sensor detects that insufficient power is directed to the plate, the controller displays a message for the user to install the plate. If the plate becomes contaminated or broken (minimum power detected), the controller displays a message to install a new plate.

Upon initial start-up, the air purifier 10 supplies full power to the purification plate 44 for a brief period of time, for example 3 to 4 seconds. The sensor measures the power communicated to the plate 44 and measures the RF, in order to detect whether the plate 44 is within operational norms. If the plate 44 is properly operational, the air purifier 10 goes to the operation mode set by the user.

If however the air purifier 10 does not become operative and the controller resets to an off condition followed by an attempt to conduct an initial start-up, the computerized controller may be experiencing interference from a defective purification plate 44. Some arcing may cause operational problems for the computerized controller. If the air purifier 10 becomes operational but resets within a predetermined period, for example, 5 seconds, the purification plate 44 is damaged. The controller then displays on the display 21 a message directing replacement of the purification plate.

The operational mode for the air purifier 10 is selectively set. This includes selecting the fan speed for a desired flow rate. The purification level based on the operation of the purification plate 44 is selectively set. The level is correlated to the square footage of coverage for the indoor area receiving the purified air. Preferably the amount of ozone generated by the purification plate 44 is not excessive for the total area of the indoor environment receiving the purified air.

The controller also provides for increased sanitation. The sanitize feature is activated with a selection button for a pre-set period of time. In the illustrated embodiment, the sanitize feature operates the purification plate 44 for selectively 2, 4, 6, or 8 hours. Upon activation of the sanitize feature, the air purifier 10 displays an indication that the system is in the sanitization mode together with the remaining time in hours and minutes for completion of the sanitation. The sanitize feature can be interrupted before the timer reaches zero.

The controller also tracks operational days for the air purifier 10. Periodically, the display will indicate that the air purifier 10 requires maintenance. This involves cleaning or vacuuming the filter element 28, cleaning the purification plate 44, cleaning the photocatalytic screen 64, and vacuuming the front and rear grill openings 16, 18. A reminder reset button clears the reminder following regular maintenance. Prior to maintenance, the power cord is detached from the power block 20.

The filter element 28 and the photocatalytic screen 64 can be cleaned with a vacuum in order to remove heavy particulates. Alternatively, the screens can be washed in hot water and brushed gently to remove particulates. Both should be dried prior to reinstallation.

The filter element 28 is removed by detaching the back cover 14. The top 30 of the filter frame 22 is removed. The filter element 28 is removed by pulling back and lifting it up and out from the arms 24 and flanges 26 that guide the travel of the filter element 28. The filter element is replaced by sliding the filter element along the arms and flanges, and fully positioning the bottom of the filter element in the seat 32. Fully seating the filter element moves the arm 86 of the contact switch 84 as discussed above.

Once the filter element 28 is removed, the purifier plate 44 and photocatalytic screen 64 are removable. The purification plate is removed by grasping an edge of the plate and gently pulling the plate from the cage 42. The purification plate 44 disengages from the contact arms 110. The photocatalytic screen 64 is slidably removed from the channel 62. After cleaning, the purification plate 44 is reinstalled by sliding into the cage in the channel 62. The photocatalytic screen 64 is reinstalled by sliding in the cage 42 and into engagement with the contact arms 110.

With the purification plate 44 and the photocatalytic screen 64 removed, the UV bulb 48 can be replaced. This is accomplished by detaching the lead wires attached to the electrical connection tabs 112 on the cage 42. Fasteners holding the cage 42 to the chassis are removed. The cage 42 is moved forwardly, lifted, and removed from the back of the housing for the air purifier 10. The starter for the UV bulb 48 can be replaced. The UV bulb 48 mounts in the socket and is readily replaced. Upon replacement of the starter and/or the UV bulb, the lead wires reattach to the tabs 112 on the purification plate cage 42.

Following reinstallation of the photocatalytic screen 64, the purifier plate 44, and the filter element 28, the back cover 14 is reattached to the front cover 12. The power cord is reconnected to the power block 20 and the air purifier 10 is ready for continued operation.

The present invention accordingly provides a air purifier featuring purification devices operated with the controller that responds to operation sensors for purifying air with interior spaces of buildings. The principles, preferred embodiments, and modes of operation of the present invention have been described in the foregoing specification. The invention is not to be construed as limited to the particular forms disclosed, as these are regarded as illustrative rather than restrictive. Moreover, variations and changes may be made by those skilled in the art without departing from the spirit of the invention described in the following claims

What is claimed is:

1. An air purifier, comprising:
   a housing with an ambient air inlet and an air outlet and defining an airflow path therethrough for treating ambient air;
   a fan for moving the air from the air inlet through the airflow path and out the air outlet;
   a filter disposed in the airflow path and having an air permeable media for communicating air therethrough while retaining particles carried in the flow of air;
   an ultraviolet light source attached to a chassis in the airflow path for treating the air with an emission of ultraviolet light, the ultraviolet light source comprises non-quartz glass through which ultraviolet light emits;
   a photocatalytic screen configured to be exposed to a light from the ultraviolet light source to create hydroxyl radicals for reacting with and neutralizing organic compounds in the flow of air;

a pair of spaced-apart arms extending from the chassis at an oblique angle relative to the air flow, the arms slidingly removingly receiving the photocatalytic screen;

a purification plate disposed in the air flow, the purification plate made of a dielectric material and opposing metal mesh screens in electrical communication with a supply of electrical current to generate an electrical spark for creating ozone in the flow of air;

an ionizer for generating a plurality of ions inserted into the airflow;

a controller for operating the air purifier;

a photocell mounted in proximity to the ultraviolet light source for being exposed to light from the ultraviolet light source, and the controller responsive to a signal from the photocell whereby the air purifier is operative during detection of light from the ultraviolet light source; and a current detector configured to sense electrical flow to the metal mesh screens of the purification plate and to signal the controller if the electrical current is below a first preselected threshold and to signal the controller if the electrical current is above a second preselected threshold, whereby the air purifier is operative if the electrical current to the purification plate is within the preselected range.

2. The air purifier as recited in claim 1, wherein the photocatalytic screen comprises a titanium oxide mesh screen.

3. The air purifier as recited in claim 1, further comprising a display configured to communicate with the controller for displaying a message regarding the status of the ultraviolet light source.

4. The air purifier as recited in claim 1, wherein the controller detects an operational status of the purification plate upon startup by applying a maximum power to the purification plate for a predetermined period and with a sensor measures a value of emitted RF which value outside an acceptable predetermined range causes the controller shutdown the operation of the air freshener.

5. The air purifier as recited claim 4, wherein upon an attempt to start operating and the controller enters a reset status within a predetermined period of time, the controller displays a message on a display for replacement of the purification plate.

6. The air purifier as recited in claim 1, wherein the ionizer comprises a needle configured to generate negative ions.

7. The air purifier as recited in claim 1, wherein the ionizer comprises an antenna configured to generate positive ions.

8. The air purifier as recited in claim 1, wherein the ionizer comprises a first ionizer configured to generate negative ions and a second ionizer configured to generate positive ions, the generated ions inserted into the flow of air communicated through the air outlet.

9. The air purifier as recited in claim 1, further comprising a frame having a detachable member for holding the air filter.

10. The air purifier as recited in claim 9, further comprising a sensor configured to monitor the positioning of the air filter within the frame and to stop communication of electrical power to the air purifier if positioning thereof is improper.

11. The air purifier as recited in claim 10, wherein the sensor comprises a switch having an arm that is contacted by an edge of the air filter when properly installed in the frame.

* * * * *